(12) United States Patent
Nalcioglu et al.

(10) Patent No.: US 9,116,216 B2
(45) Date of Patent: Aug. 25, 2015

(54) MR COMPATIBLE COMPRESSION BASED NUCLEAR IMAGING SYSTEM FOR BREAST CANCER

(75) Inventors: Orhan Nalcioglu, Newport Coast, CA (US); Werner W. Roeck, Irvine, CA (US)

(73) Assignee: The Regents of the University of California, Oakland, CA (US)

( * ) Notice: Subject to any disclaimer, the term of this patent is extended or adjusted under 35 U.S.C. 154(b) by 156 days.

(21) Appl. No.: 13/604,564

(22) Filed: Sep. 5, 2012

(65) Prior Publication Data

US 2012/0330131 A1 Dec. 27, 2012

Related U.S. Application Data

(63) Continuation-in-part of application No. 12/763,863, filed on Apr. 20, 2010, now abandoned.

(60) Provisional application No. 61/540,473, filed on Sep. 28, 2011.

(51) Int. Cl.
| | |
|---|---|
| *A61B 5/055* | (2006.01) |
| *G01R 33/48* | (2006.01) |
| *G01R 33/34* | (2006.01) |
| *A61B 6/03* | (2006.01) |
| *A61B 6/00* | (2006.01) |

(52) U.S. Cl.
CPC .............. *G01R 33/481* (2013.01); *A61B 6/037* (2013.01); *G01R 33/34061* (2013.01); *A61B 6/583* (2013.01)

(58) Field of Classification Search
CPC .. A61B 6/037; A61B 6/583; G01R 33/34061; G01R 33/481
See application file for complete search history.

(56) References Cited

U.S. PATENT DOCUMENTS

| | | | | |
|---|---|---|---|---|
| 2008/0125643 | A1* | 5/2008 | Huisman et al. | 600/420 |
| 2009/0105582 | A1* | 4/2009 | Dougherty et al. | 600/420 |
| 2013/0137964 | A1* | 5/2013 | Schellenberg | 600/411 |

FOREIGN PATENT DOCUMENTS

WO WO 2010079251 A1 * 7/2010

* cited by examiner

*Primary Examiner* — Ruth S Smith
(74) *Attorney, Agent, or Firm* — Knobbe, Martens, Olson & Bear, LLP

(57) ABSTRACT

An apparatus combines magnetic resonance (MR) and nuclear imaging of human breast for cancer diagnosis. An MRI system including an MR breast RF coil is combined with a nuclear imaging system having a detector disposed or disposable within the MR breast RF coil arranged and configured for the performance of simultaneous or sequential coregistered breast MRI and nuclear imaging. A selectively controlled compression mechanism for lightly compresses the breast being imaged. The remotely controlled compression mechanism is integrated with the MR breast RF coil.

10 Claims, 14 Drawing Sheets
(9 of 14 Drawing Sheet(s) Filed in Color)

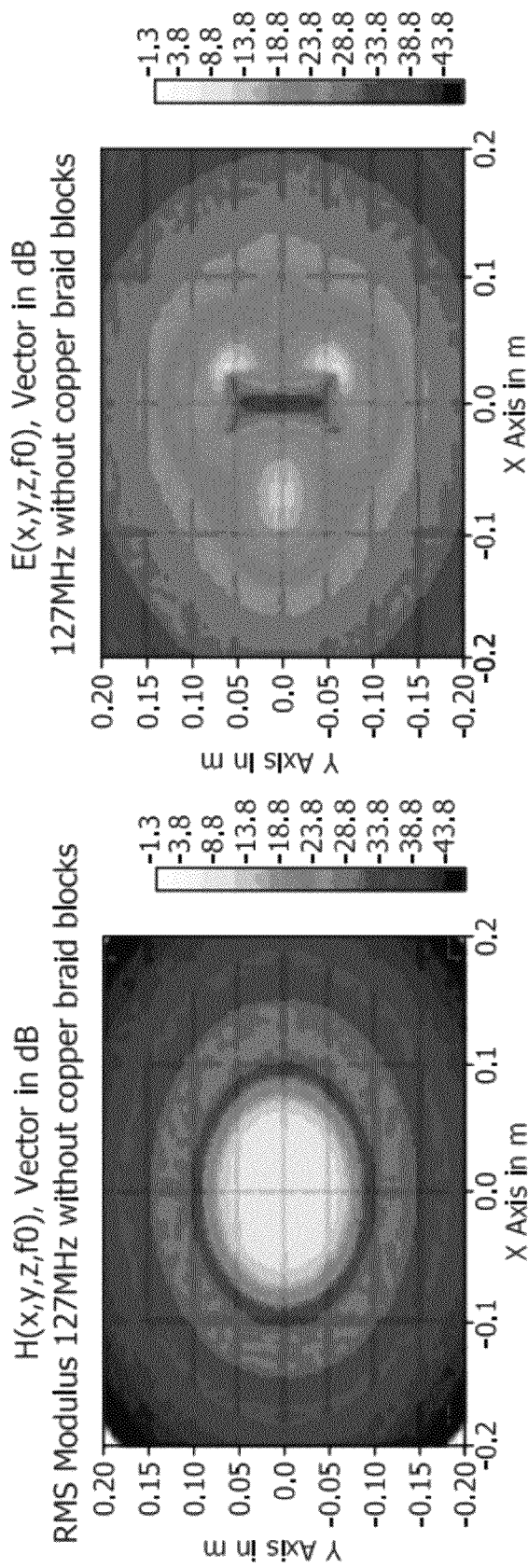

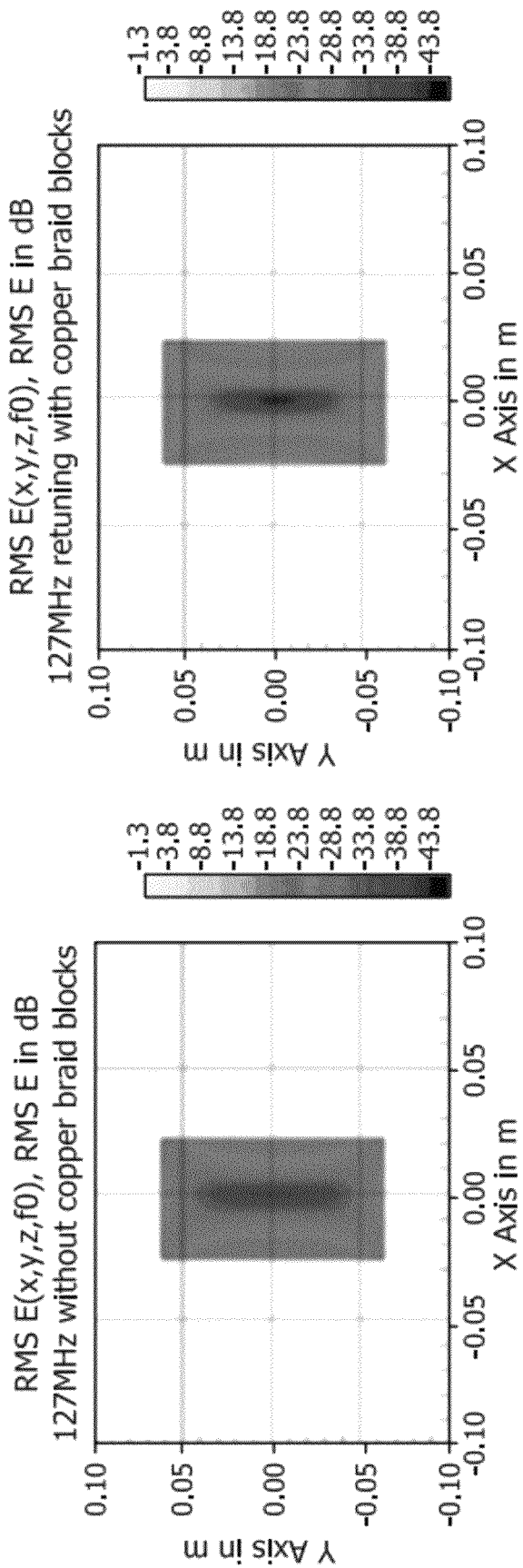

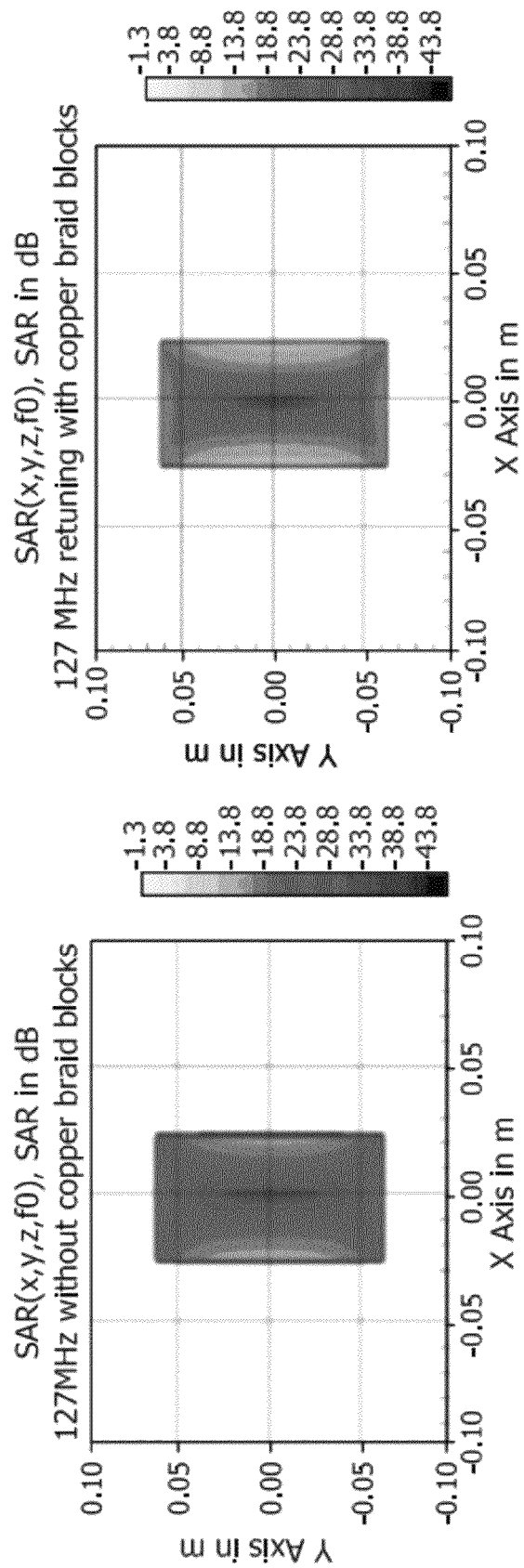

MR COMPATIBLE COMPRESSION BASED NUCLEAR IMAGING SYSTEM FOR BREAST CANCER

RELATED APPLICATIONS

The present application is related to U.S. Provisional Patent Application Ser. No. 61/540,473, filed on Sep. 28, 2011 pursuant to 35 USC 119 and is a continuation in part of U.S. patent application Ser. No. 12/763,863 filed on Apr. 20, 2011 pursuant to 35 USC 120, both of which are incorporated herein by reference.

FIELD OF THE INVENTION

This invention relates generally to multi-modal medical imaging, and more specifically to the use of combined magnetic resonance-single photon or positron emission tomography of the human breast for diagnosis of cancer and evaluation of treatment.

BACKGROUND

Although mammography is very sensitive in detecting early breast cancer, it does not work well in women who have dense breasts, breast implants, or scar tissues. Alternatively, magnetic resonance imaging (MRI) has proven to the most sensitive imaging modality in delineating tumor extent and detecting multifocal or multicentric diseases. Many studies indicate that preoperative MRI is useful in local staging for surgical planning, especially for patients with lobular cancer. However, the variable specificity of MRI can lead to unnecessary biopsies and over-treatment.

Scintimammography (SMM) is a single photon breast imaging technique used to detect cancer cells in patients who have had abnormal mammograms or dense breast tissue. In this test, a patient will receive an injection of technetium 99 sestamibi, a gamma-ray emitter which is preferably taken up by cancer cells. The breast is then usually compressed and imaged by a gamma camera. SMM can potentially supplement MRI for improving the diagnostic specificity in breast cancer imaging.

The combination of MRI and SMM has great clinical potential for improving specificity through SMM while maintaining the high sensitivity offered by MRI. However, interference between the MRI and SMM components presents a significant challenge to the design of any combined system. This interference can lead to major artifacts and image degradation in both modalities. The primary concerns are electromagnetic interference and the effects of the $B_0$ magnetic field of the MRI scanner on the SMM detectors. Traditional gamma-ray detectors based on scintillators coupled to photomultiplier tubes do not function properly within high magnetic fields. Instead, MR-compatible cadmium-zinc-telluride (CZT) semiconductor-based radiation detectors may be utilized. Such detectors, however, must be enclosed in RF shielding to prevent electromagnetic interference between the MRI and SMM systems. Furthermore, sufficient gamma-ray shielding is required to prevent the detection of uncollimated radiation. Both of these shielding layers have the potential to adversely affect MR imaging, particularly when they are placed within the RF coil.

BRIEF SUMMARY OF THE INVENTION

To solve these and other long-felt needs in the art, an apparatus and method for MRI-compatible nuclear breast cancer imaging is here disclosed. In its primary aspect, the illustrated embodiments of the invention include a MR breast RF coil combined with planar scintigraphic or PET detectors to enable one to perform coregistered breast MRI and nuclear imaging. This technique has been termed magnetic resonance-scintimammography (MRSMM). If PET detectors are used then it is called positron emission mammography (PEM). In case of the positron emission version of the same device single photon detectors such as CZT are replaced by MR compatible positron emission coincidence detectors. When dedicated positron emission tomography is used for breast imaging it is called positron emission mammography (PEM). The RF coil and compression device described in this application is equally applicable to SMM as well as PEM with appropriate replacement of the detectors.

One embodiment of the invention, the MR-SSM or MR-PEM apparatus, comprises an MRI imaging system having an RF array coil consisting of two parallel circular loops, each mounted on an acrylic end plate with the material normally found within MRI loops removed to allow for insertion of the breast. The ea of separation between the end plates allows for the insertion of opposing CZT detector modules with parallel-hole collimators, integrated with breast compression paddles. The opposing CZT detector modules are part of a nuclear imaging system. A control device allows for accurate adjustment of the compression of the breast by the paddles under observation. In case of PEM the CZT detectors are replaced by the PEM detectors while the remainder being the same.

In another embodiment the invention comprises a method of use for the apparatus. The RF coil is positioned within an MRI bore such that it generates a $B_1$ magnetic field parallel to the (vertical) y-axis. The patient lies prone on top of the assembly with the breast to be imaged inside the RF array coil, and is injected with the appropriate radiopharmaceutical without being moved from the RF coil. After a short period of time, the CZT detector module integrated with breast compression paddles are brought towards the breast in question and the breast is compressed lightly using a selectively controlled compression device. The MR/SMM or MR/PEM assembly, including the RF coil, can be adjusted along the y-direction so that the volume of interest within the breast can be centered within the RF coil and positioned within the field of view of the CZT detectors. The assembly may rotate around the y-axis around the breast, and MR images may be used to determine the optimum orientation of the CZT detectors.

In particular, the illustrated embodiments include an apparatus for combined magnetic resonance (MR) and nuclear imaging of human breast for cancer diagnosis comprising an MRI system including an MR breast RF coil combined with a nuclear imaging system having a detector disposed or disposable within the MR breast RF coil arranged and configured for the performance of simultaneous or sequential coregistered breast MRI and nuclear imaging, and a selectively controlled compression mechanism for lightly compressing the breast being imaged in which the compression mechanism is integrated with the MR breast RF coil.

The detector of the nuclear imaging system includes a scintigraphic single photon imager or coincidence based positron emission tomography (PET) detector.

The mechanism for lightly compressing the breast being imaged includes a pair of opposing compression paddles and where the detector of the nuclear imaging system comprises a pair of opposing rectangular nuclear detectors placed behind the compression paddles in either side away from the breast, which is placed between the compression paddles.

The detector of the scintigraphic nuclear imaging system (SMM) includes a pair of opposing cadmium-zinc-telluride (CZT) detectors each encapsulated in RF and gamma-ray shielding and disposed within the MR breast RF coil. For PEM appropriate MR compatible positron coincidence detection detectors are used.

The MR breast RF coil includes a pair of opposing RF coils aligned on a common axis and separated by an open space, and where the detector of the nuclear imaging system comprises a pair of opposing rectangular nuclear detectors oriented on a common axis perpendicular to the common axis of the pair of opposing RF coils.

In one embodiment the opposing rectangular nuclear detectors are permanently disposed into the open space between the pair of opposing RF coils.

In another embodiment the opposing rectangular nuclear detectors are movable to be temporarily disposed into the open space between the pair of opposing RF coil's when a nuclear image is being taken.

The nuclear detector is gamma shielded and RF shielded and further comprising a collimator disposed between the breast and the detector for collimating nuclear radiation from the breast to the detector.

The illustrated embodiments also encompass a method for use in diagnostic breast imaging of a subject including the steps of positioning the subject in a prone position into a breast MR RF coil in an MRI system to image a selected breast, performing a dynamic contrast enhanced MRI on the selected breast, if the selected breast shows any increased signal enhancement, then injecting the subject with a selected radiopharmaceutical without moving her from the MRI imaged position in the MR RF coil, and employing a nuclear detector, inside the MR RF coil, to image the selected breast while applying light breast compression to the selected breast in a predetermined direction during imaging.

The method is also performed on the other one of the breasts other than the selected breast.

The method employs a nuclear detector, inside the MR RF coil, to image the selected breast comprises using MR-single photon scintigraphy or MR-PEM for imaging.

The illustrated embodiments of the invention are also defined as a method use in diagnostic imaging of a human breast for cancer diagnosis including the steps of performing scintimammography (SMM) or positron emission mammography (PEM), and performing MRI to improve the diagnostic specificity and to result in both high sensitivity from MRI and high specificity from SMM or PEM by using a dual-modality system with an ntegrated radio frequency (RF) coil and radiation detector under a strong magnetic field without significant mutual interference.

The combination of performing scintimammography (SMM) or positron emission mammography (PEM) and performing MRI uses a unilateral breast array MR RF coil specialized for combined MRI and nuclear imaging.

The combination of performing scintimammography (SMM) or positron emission mammography (PEM) and performing MRI includes simultaneously acquiring MR and SMM or PEM images of a breast using an integrated MR-SMM or MR-PEM system as appropriate.

The illustrated embodiments include a composite data image recorded on a tangible medium produced by performing scintimammography (SMM) or positron emission mammography (PEM) and by performing MRI to improve the diagnostic specificity and to result in both high sensitivity from MRI and high specificity from SMM or PEM by using a dual-modality system with an integrated radio frequency (RF) coil and radiation detector under a strong magnetic field without significant mutual interference in which data image is a composite of a coregistered MRI image and a nuclear image. The composite data in age is generated by conventional overlay imaging software well known to the art for combining and coregistering two data fields, one for the MRI and the other from SMM or PEM.

While the apparatus and method has or will be described for the sake of grammatical fluidity with functional explanations, it is to be expressly understood that the claims, unless expressly formulated under 35 USC 112, are not to be construed as necessarily limited in any way by the construction of "means" or "steps" limitations, but are to be accorded the full scope of the meaning and equivalents of the definition provided by the claims under the judicial doctrine of equivalents, and in the case where the claims are expressly formulated under 35 USC 112 are to be accorded full statutory equivalents under 35 USC 112. The disclosure can be better visualized by turning now to the following drawings wherein like elements are referenced by like numerals.

BRIEF DESCRIPTION OF THE DRAWINGS

The specification contains at least one drawing executed in color. Copies of this patent or patent application publication with color drawing(s) will be provided by the Office upon request and payment of the necessary fee.

FIGS. 3a-3f are colored two dimensional data graphs of the simulated RMS modulus $B_1$ field distribution (left column) and RMS modulus $E_1$ electric field distribution (right column) generated by the RF array coil tuned to 127 MHz without the phantom conductive copper blocks (FIGS. 3a, 3b), the coil shifted to 138 MHz with the introduction of the phantom conductive blocks (FIGS. 3c, 3d), and coil with the conductive blocks re-tuned to 127 MHz (FIGS. 3e, 3f). The phantom copper blocks were hollow brick shaped Lucite phantoms filled with a copper sulfate solution. A shift in the electric field intensity around discrete components such as capacitors accounts for the asymmetry in FIG. 3b. The $B_1$ field maps were normalized to $2.37 \times 10^{-10}$ A/m and the electric field maps ere normalized to $2.59 \times 10^{-8}$ V/m.

FIGS. 4a-4f are colored two dimensional data graphs of the simulated $B_1$ field distribution (FIGS. 4a, 4b), $E_1$ electric field distribution (FIGS. 4c, 4d) and SAR distribution (FIGS. 4e, 4f) generated by the RF array coil tuned to 127 MHz without the phantom conductive copper blocks (left column) and with the phantom copper blocks (right column). The $B_1$ maps were normalized to $2.37 \times 10^{-10}$ A/m, the electric field maps were normalized to $2.59 \times 10^{-8}$ V/m and the SAR maps were normalized to $5.48 \times 10^{-20}$ mW/g.

FIGS. 6a-1-6d-4 are grayscale data MR images of the brick phantom with no shielding (FIGS. 6a-1 to 6a4), RF shielding (FIGS. 6b-1 to 6b4), gamma-ray shielding (FIGS. 6c-1 to 6c-4) and both shielding (FIGS. 6d-1 to 6d-4) placed 10 mm from the phantom within the RF coil. All modulus and phase images were each scaled to identical contrast levels.

The disclosure and its various embodiments can now be better understood by turning to the following detailed description of the preferred embodiments which are presented as illustrated examples of the embodiments defined in the claims. It is expressly understood that the embodiments as defined by the claims may be broader than the illustrated embodiments described below.

DETAILED DESCRIPTION OF THE INVENTION

Figure 1A:
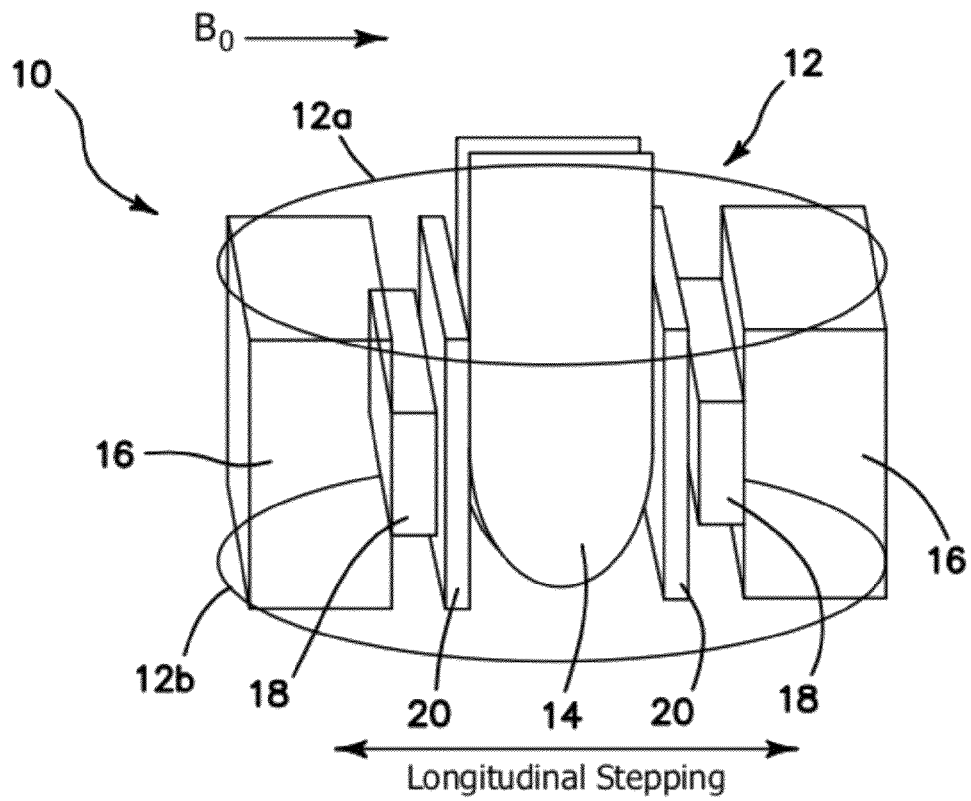
FIG. 1a is a simplified diagram of the material elements internal to the MRSMM assembly.
Figure 1B:
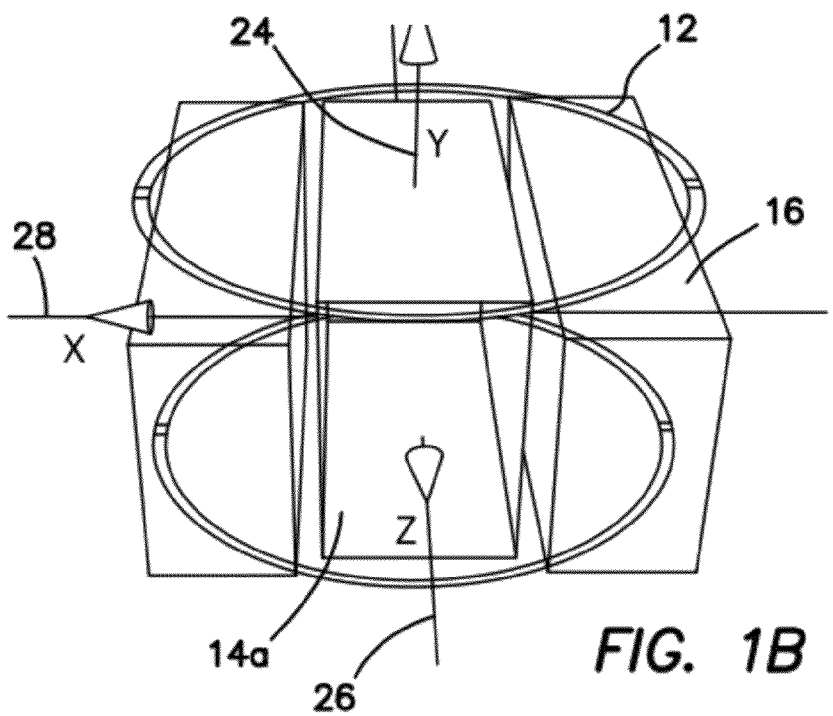
FIG. 1b is a three dimensional rendering of a model of the RF coil and RF shielded detector blocks for use in a simulation program, which blocks are located 10 mm from a brick-shaped phantom.

One embodiment of the present invention is the MRSSM apparatus 10. One preferable embodiment of apparatus 10 is optimized for a 3T magnetic resonance imaging (MRI). However, it is to be understood that any conventional MRI field specification or MRI imaging system may be employed, when modified as disclosed below. The geometry of the RF array coil 12 of the MRI system includes two parallel circular loops 12a and 12b each 15 cm in diameter and separated by 6.5 cm as diagrammatically shown in FIG. 1a. In the illustrated embodiment as an example only, each loop 12a and 12b is etched on FR4 laminate board using copper strips of 0.0341 mm thickness, and mounted on an acrylic plate with the material within the loops removed to allow for insertion of the breast 14. The separation between the end plates of the coils 12a and 12b allows for insertion of CZT detector modules 16 through the side of the RF coil 12. MR compatible CZT detector modules 16 have been developed with the consultation of the inventors by Gamma Medica Inc. Each coil loop 12a, 12b also contained fully integrated components that are tuned to 127 MHz (the Larmor frequency at 3T) and matched to 50Ω. A collimator 18 is provided inwardly of each CZT detector module 16 adjacent to paddles 20 used for compression of breast 14. The mechanism for selectively controlling the positioning and force applied to paddles 20 may assume any one of many different conventional configurations well known to the art. FIG. 1b is a rendering of a simulation model of a breast phantom 14a between detector modules 16 and between coils 12a, 12b, showing the x axis 28, y axis 24 and z axis 26.

Mutual coupling between the coils 12a, 12b cannot be eliminated by geometrical overlapping or connecting to low noise amplifiers alone. Thus to remove mutual coupling, two methods are simultaneously used: Inductive decoupling, in which air inductors (not shown) are connected to each coil loop 12a, 12b are crossed over, and integration of low noise amplifiers (not shown) with a low input impedance (below 20Ω). Since the RF array coil 12 operates only as a receiver, the above combined detuning method using active and the passive detuning circuits added to each loop 12a, 12b was utilized to decouple the array coil 12 during transmission of high power RF energy.

Figure 1C:
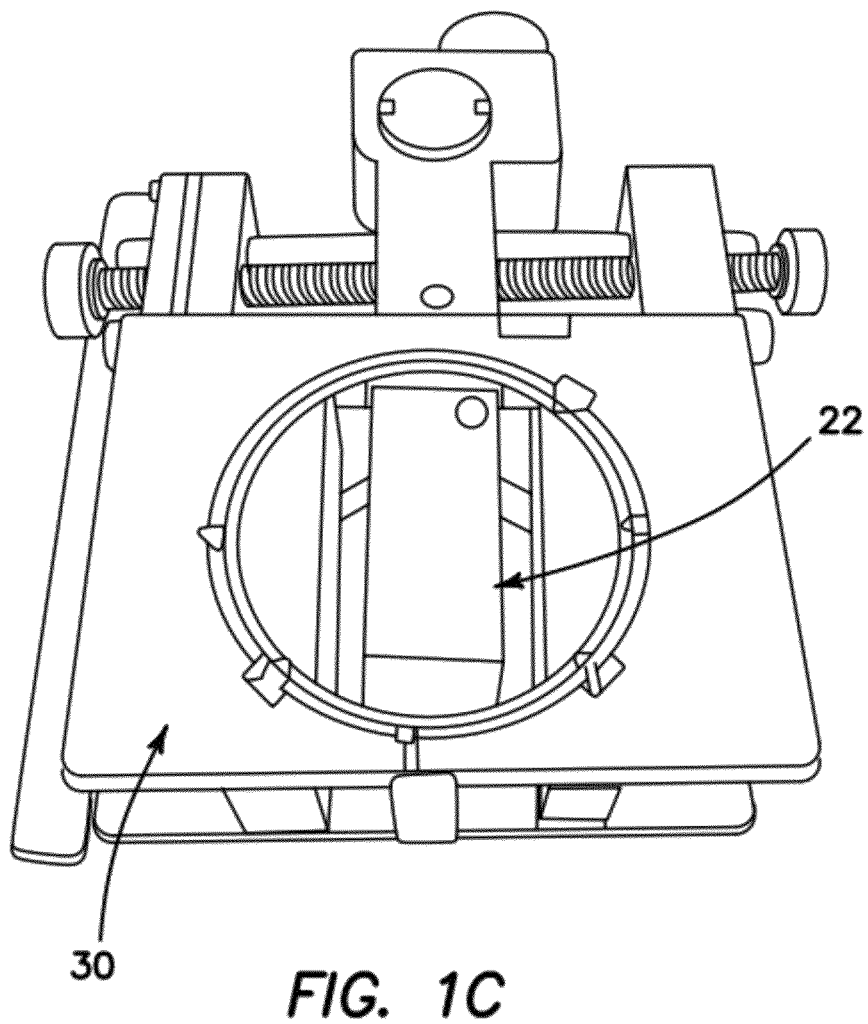
FIG. 1c is a top down view of are experimental setup for testing RF and gamma-ray shielding in the RF coil.
Figure 1D:
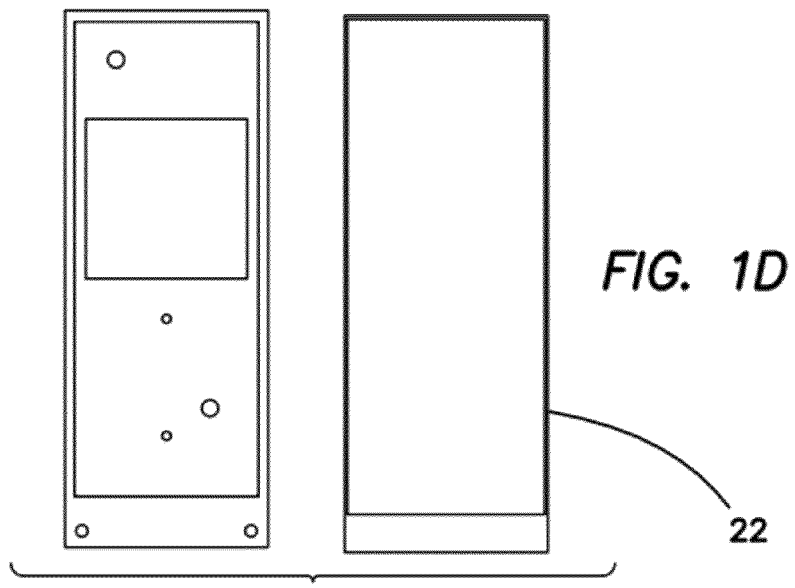
FIG. 1d is a top down view of a gamma-ray shielding box on the left and an additional RF shielding on the right of the photograph.
Figure 2A:
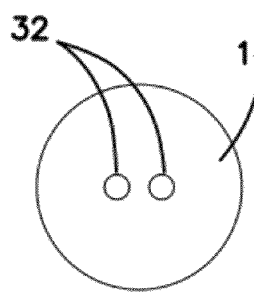
FIG. 2a-2d is a diagram of breast compression at an uncompressed state, 0°, 45°, and 90° compression angles respectively.
Figure 2B:
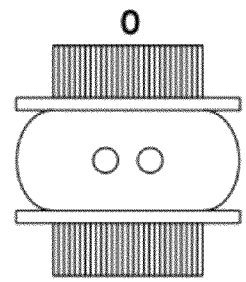
Figure 2C:
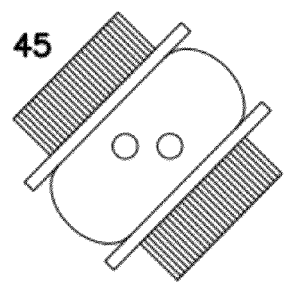
Figure 2D:
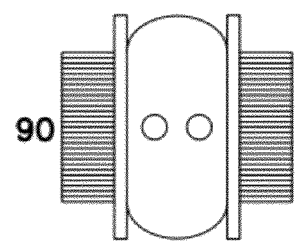

For SMM imaging, each CZT-based radiation detector module 16 (Gamma Medica, Inc., Northridge, USA) including a 50.8×50.8×5 mm of CZT crystal coupled to 1024 (32×3) detector elements is mounted in a 17×6.5×6 mm box 22. The walls of box 22 are made of a lead composite for gamma-ray radiation shielding. The MR compatibility of the lead composite when placed outside of an RF coil 12 has been demonstrated in the prior art. The lead composite of the walls of box 22 is segmented on the edges to suppress the flow of eddy currents caused by gradient switching in the MRI, which may prevent significant image artifacts in MRI such as image distortion. The box 22 of FIG. 1d is experimentally tested for RF and gamma-ray shielding using the experimental jig 30 of FIG. 1c.

For breast imaging, two opposing CZT detector nodules 16 with parallel-hole collimators 18 are integrated with breast compression paddles 20 and positioned between the acrylic end plates (not shown) of the RF coil 12. A control knob (not shown) is mechanically coupled to paddles 20 to allow for accurate adjustment of the compression under observation by the operator. Although breast compression is not required for MR imaging, it is of benefit to SMM since this modality's spatial resolution decreases as the distance of a human breast 14 from the collimator 18 increases. While the use of opposing detectors 16 can compensate for this resolution loss on the periphery, compression is needed to reduce the distance from the center of the breast 14 to each collimator 18.

The RF coil 12 is positioned within the MRI bore (not shown) such that it generates a $B_1$ magnetic field parallel to the y-axis. The MRSMM assembly 10 including the RF coil 12 may be adjusted along the vertical y-direction so that the volume of interest within the breast 14 can be centered within the RF coil 12 and positioned within the field-of-view (FOV) of the CZT detectors 16. Furthermore, the assembly 10 may rotate about the y-axis 24 around the breast 14. This feature is important for SMM imaging when distinguishing multiple lesions. Unlike three-dimensional (3D) tomography, SMM only acquires two dimensional (2D) projection images. Thus in the case of two lesions, one orientation provides maximum separation while others make it difficult to distinguish. An immediate benefit of combined MRSMM imaging is that the MR images can be used to determine the optimum orientation of the CZT detectors 16.

The RF coil 12 for MRSMM imaging should provide high signal-to-noise (SNR) and field homogeneity in the presence of the CZT detector modules 16. However, these modules 16, particularly the RF shielding, may distort the EM field generated by the RF coil 12. In a prior art study of this distortion, the system configuration allowed for the RF shielding to be placed up to 6 cm away from the RF coil. Therefore, the $B_1$ field and parameters, such as the quality (Q) factor, resonance frequency, and impedance of the RF coil were not significantly affected. In the illustrated embodiments of the invention, the CZT detector modules 16 are positioned directly between the end plates of the RF coil 12. Due to the close proximity of these components, the effect of the RF shielding on the RF coil 12 requires investigation. To investigate this issue, the RF coil 12 and RF shielding were modeled using a simulation program (SEMCAD X Ver, 14.2.1, Schmid & Partner Engineering AG, Zurich Switzerland) to assess the EM field change, resonance frequency variation, and SAR distribution when the detector modules 16 were positioned through the side opening of the RF coil 12. Specific absorption rate (SAR) is a measure of the rate at which energy is absorbed by the body when exposed to a radio frequency (RF) electromagnetic field; although, it can also refer to absorption of other forms of energy by tissue, including ultrasound. It is defined as the power absorbed per mass of tissue and has units of watts per kilogram (W/kg). SAR is usually averaged either over the whole body, or over a small sample volume (typically 1 g or 10 g of tissue). The value cited is typically then the maximum level measured in the body part studied over the stated volume or mass.

While the actual RF shielding consists of copper mesh covering the detector modules 16, it was modeled as perfect conductive blocks with electric conductivity $a=5.96\times10^7$ S/m in the simulation. The SAR map was calculated as:

$$SAR=(\sigma/2\rho)|E|^2$$

Where $\rho$ is the mass density of the object and E is the induced electric field vector which was calculated using the finite difference time domain method. To simulate a compressed breast 14, a 11.5×11.6×4.5 cm brick-shaped dielectric phantom 14a was used with the following parameters: relative permittivity $(\in_r)=32.6$, electric conductivity $(\sigma)=0.61$ S/m and density=1000 kg/m$^3$.

Changes in the Q-factor, resonance frequency, and impedance when the CZT detectors 16 are positioned within the system may be evaluated using the RF array coil 12. These parameters may be measured with the CZT detector modules 16 placed at various distances from the isocenter of the RF coil 12. The modules 16 may be tested without RF and gamma-ray shielding, with RF shielding only, with gamma-ray shielding only, and with both RF and gamma-ray shielding. All parameters may be measured without loading the RF coil 12.

A brick-shaped phantom 14a with identical dimensions to the simulation was used for MRI tests. It was filled with a solution of 4.0 g/L CuSO$_4$.5H$_2$O, 10 g/L NaCl, and distilled water. The phantom was positioned at the isocenter of the RF coil 12 and the detector modules 16 positioned 10 cm away from the phantom 14a. The setup was placed within a 3T Philips Achieva system (Philips medical Systems, Netherlands). Coronal MR images of the middle of the phantom 14a were acquired using a gradient-echo sequence with the parameters: FOV=120×120 mm, matrix size=256×256, echo time (TE)=5 ms, repetition time (TR)=30 ms, flip angle=60°, slice thickness=5 mm, and number of signal averages (NSA)=4. MRI data was acquired for detector modules 16 without RF and gamma-ray shielding, with RF shielding only, with gamma-ray shielding only, and with both RF and gamma-ray shielding. For each configuration, MR images were acquired without and with $2^{nd}$ and $3^{rd}$ order shimming to assess correction of any $B_0$ field distortions caused by the shielding.

From the acquired MRI, the signal-to-noise ratio (SNR) was calculated as [(signal average−noise average)/(noise standard deviation)]. To measure the phantom signal, a rectangular region of interest was drawn over the central 80% of the phantom image. To calculate the noise, the standard deviation was measured from the background.

To demonstrate operation of the integrated MRSMM system 10, simultaneous MR and SIMM imaging of a breast phantom 14a were performed. A hollow, oval-shaped acrylic cylinder with a length of 80 mm, width of 68 mm, and height of 120 mm was used to simulate a compressed breast 14. Two vials 32 of 10 mm in diameter each and separated by 15 mm were used to simulate breast lesions. The phantom 14a was placed at the center of the RF coil 12 within a 3T MRI system. The two vials 32 simulating lesions were placed at the center of the phantom 14a. Three different orientations for the vials 32 were tested (0°, 45°, 90° simulating three different angles of breast compression as diagrammatically shown in FIGS. 2a-2d. Three different data sets may acquired, each testing the three different orientations for the vials 32. For all data sets, the vials 32 were each filled with a solution of 4 mM CuSO$_4$ and 60 µCi/ml of $^{99m}$Tc sestimibi (Cardiolite; Cardinal Health, Dublin, USA) as a pharmaceutical agent used in nuclear medicine imaging. For the first data set, a hollow breast phantom 14a "background" was left empty. In the second data set, the background was filled with a 10 mM CuSO4 solution. In the third data set, the background was filled with a solution containing both 10 mM CuSO$_4$ and 1 µCi/mL of $^{99m}$Tc sestimibi. For each vial orientation, a coronal MR image of the middle of the phantom 14a was acquired using a 20 fast-spin-echo sequence with the following parameters: TR=1.5 s, TE=80 ms, FOV=150×150 mm, matrix=512×512, slice thickness=5 mm, NSA=4. Concurrent to the MRI acquisition, nuclear radiation counts were recorded from the CZT detector modules 16 for 10 minutes. The spectrum for each detector modules 16 was then windowed about the 140 keV photopeak (±5%) and the resulting SMM images were adjusted for radioactive decay and corrected for inherent nonuniform detector sensitivity using the image of a flood-field phantom. For the 0° orientation, a ROI was drawn about one of the vials 32 in each of the SMM images. The number of radiation counts within the ROI was then computed. From the MR image, the distance from the vials 32 to the detector module 16 through the background was measured. This information was then used to correct for attenuation by the water background in the second and third data sets. In the SMM images of the third data set, a second ROI containing only the background along with geometrical measurements from the MR images was used to determine the background activity concentration. This information was used to remove the background contribution to the counts measured within the first ROI prior to attenuation correction. After this background correction, attenuation correction was then performed to yield the corrected activity of only the vial 32.

Figures 3C, 3D:
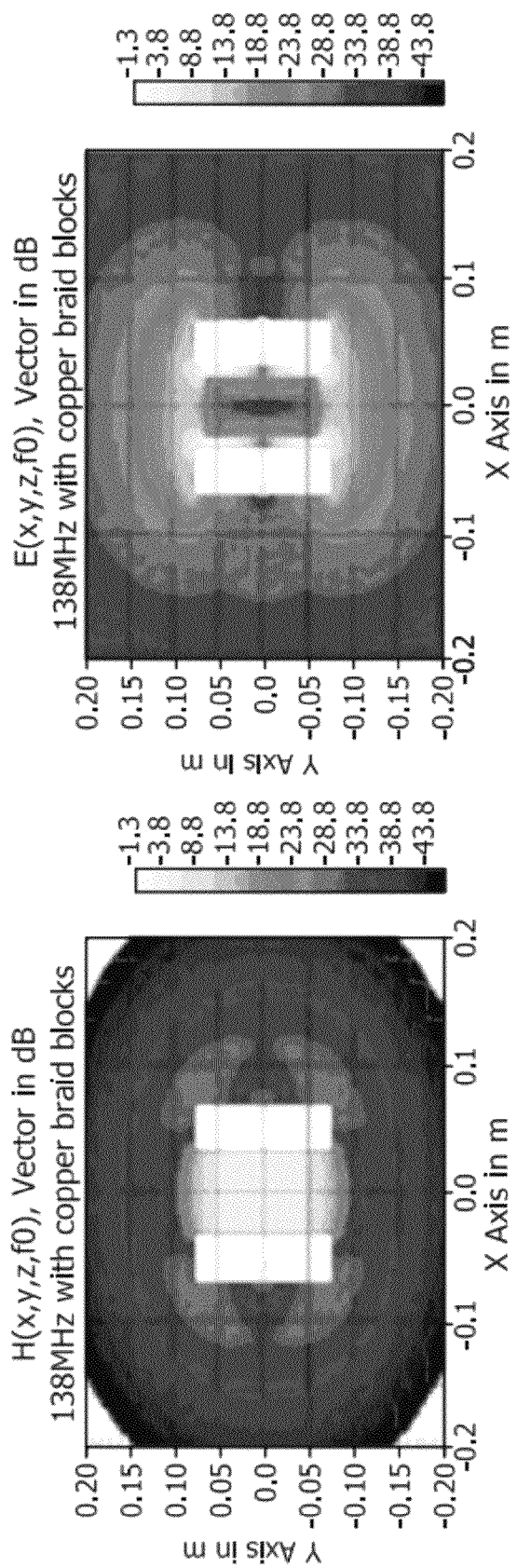
Figures 3E, 3F:
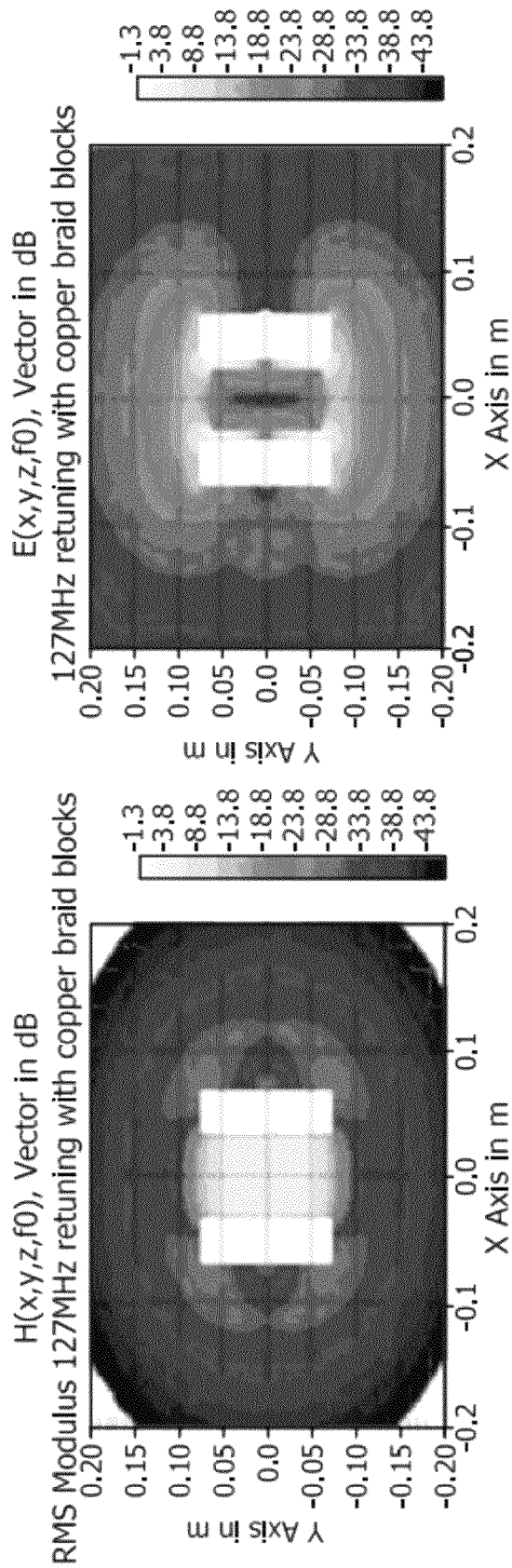
Figures 4A, 4D:
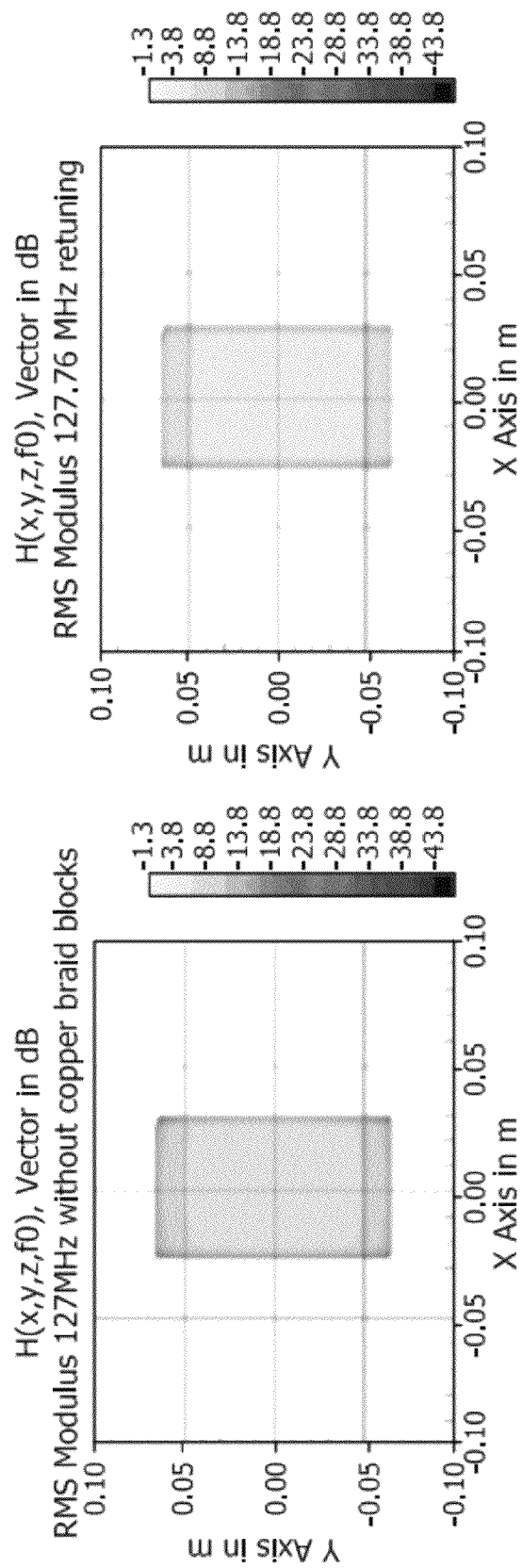

In simulation studies, the RF array coil 12 tuned exactly to the target frequency (127 MHz) without the presence of the RF-shielded modules 16 was observed to have generated a homogeneous $B_1$ field in the region between the coil loops 12a, 12b as shown in FIGS. 3a and 4a. With the addition of the conducting blocks, the resonance frequency of RF coil 12 shifted to 138.2 MHz. Nevertheless, at this shifted frequency, the conducting blocks did not produce any $B_1$ field distortion within the phantom region as shown in FIGS. 3c and 4d. In contrast, the root mean square (RMS) $E_1$ electric field sharply increased near the surface of the conducting blocks as shown in FIGS. 3d and 4e. After re-tuning the RF coil 12 back to the target frequency with the conductive blocks present, the $B_1$ field within the phantom 14a remained uniform while its intensity slightly increased compared to the field generated by the RF coil 12 without the conducting blocks. The RMS $E_1$ electric field intensity on the surface of the phantom 14a remained higher than the other areas due to electric charges concentrated on the surface of phantom conductive copper blocks. As a result, a high SAR was localized on the surface of the phantom 14a as shown in FIG. 4f.

Figure 5A:
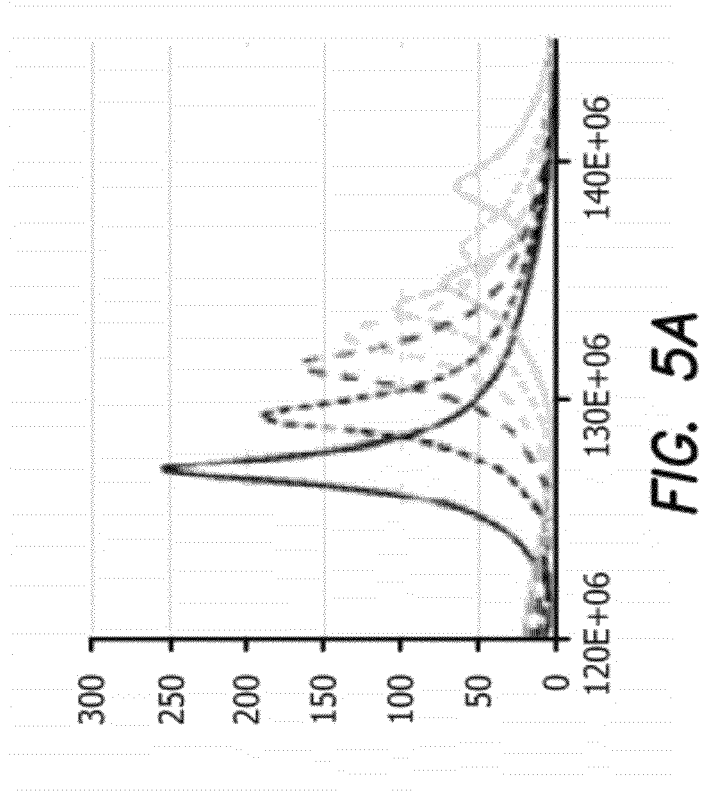
FIGS. 5a-5f are colored graphs of the frequency spectra (impedance in Ω versus frequency in MHz) of the RF array coil with the RF shielding (FIGS. 5a, 5b), gamma-ray shielding (FIGS. 5c, 5d) and both shielding (FIGS. 5e, 5f) placed 125 mm (black solid line), 85 mm (black dotted line), 52 mm (black dashed line), 42 mm (gray dashed line), 36 mm (gray dotted line), 26 mm (gray solid line), and 26 mm with re-tuning (red line) from the isocenter of the coil.
Figure 5B:
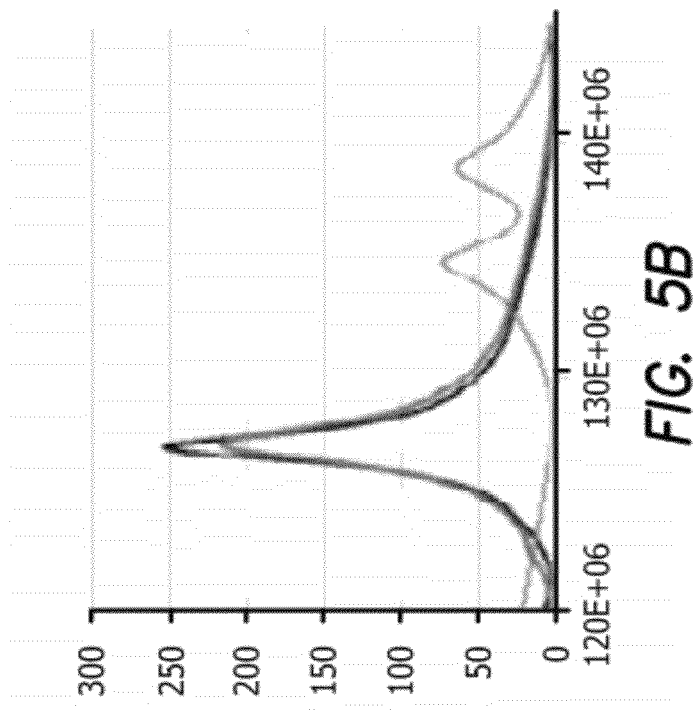
Figures 5C, 5D:
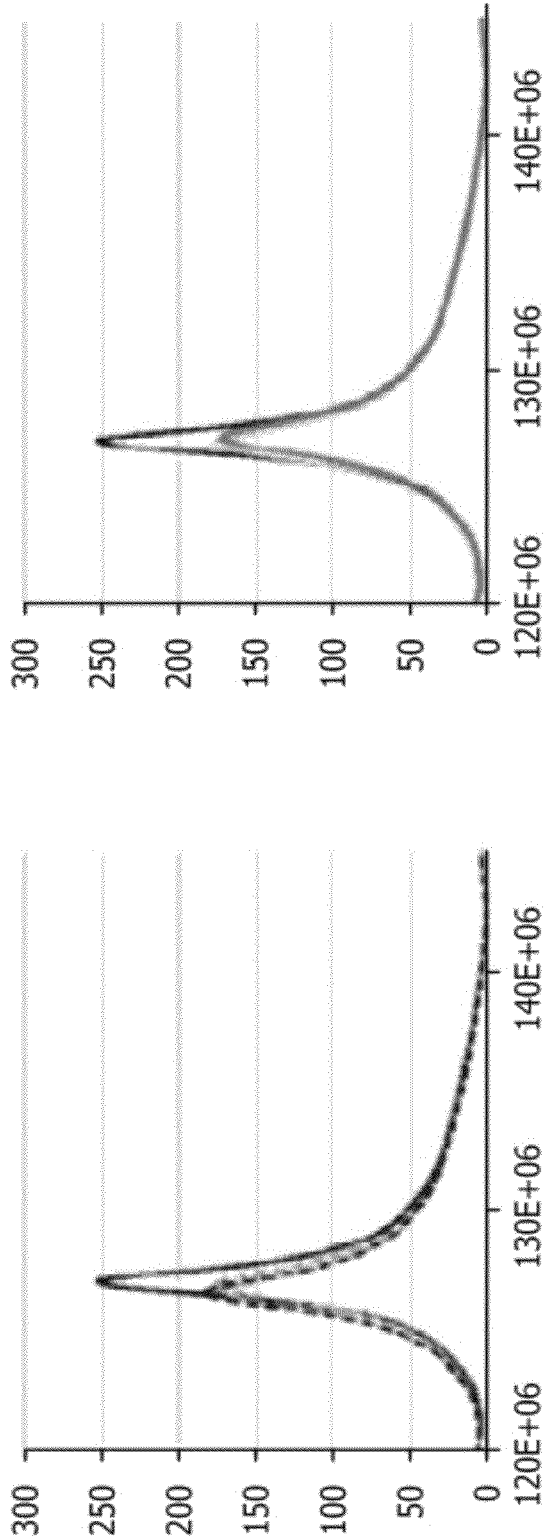
Figure 5F:
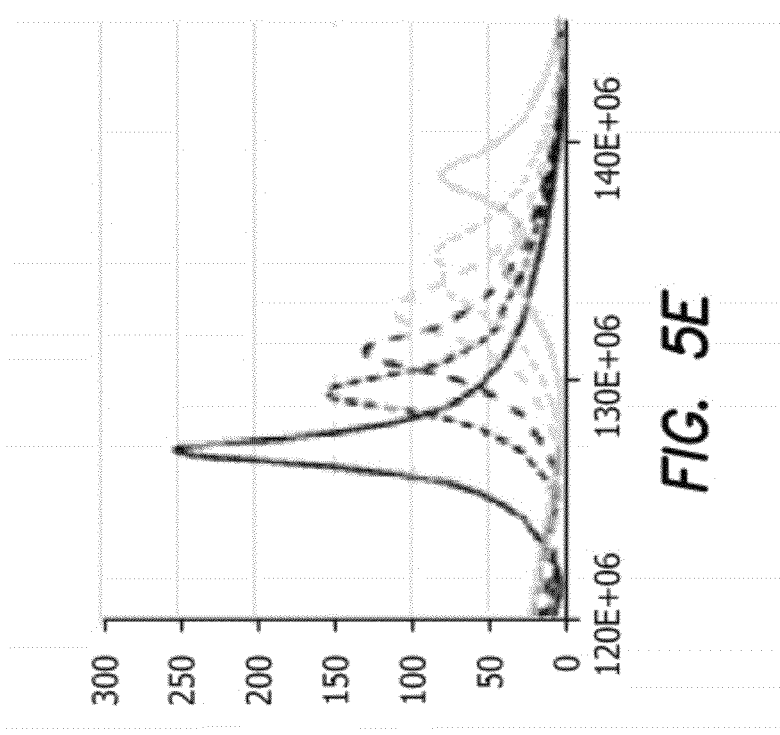
Figure 5E:
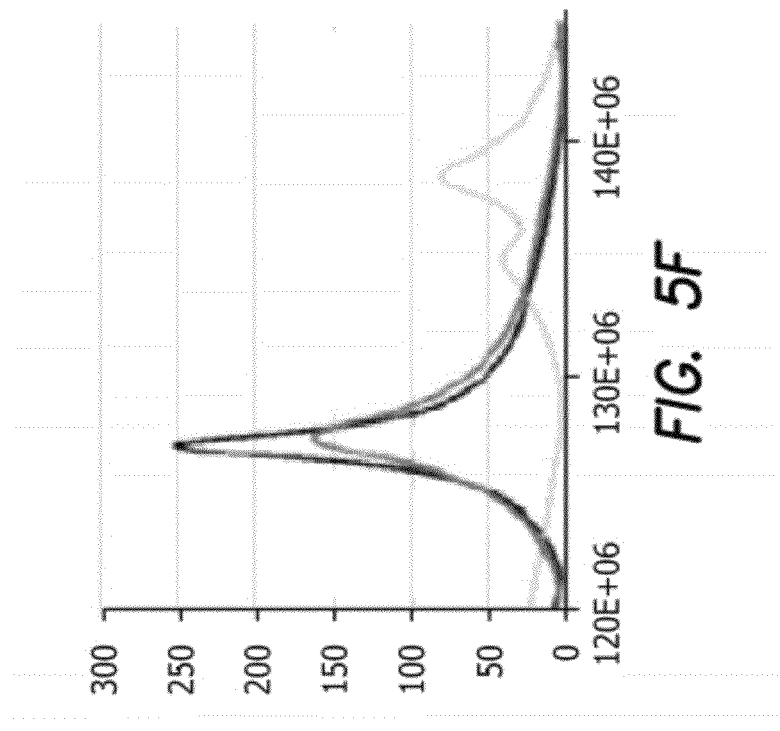

The Q-factors and impedances for each of the two circular loops 12a, 12b of the RF array coil 12 may be experimentally measured without the presence of any shielding. In one embodiment, Q-factor and impedance of the top loop 12a was 118.6 and 251.6Ω respectively, while the measurements for the bottom loop 12b were 116.8 and 247.0Ω. When the RF-shielded modules 16 (without gamma-ray shielding) were placed 10 mm away from the phantom 14a (26 mm from the isocenter of the RF coil 12), the Q-factor and impedance of both coil loops 12a, 12b decreased 27.1% and 46.3% respectively. The resonance frequency also shifted up about 6.5 MHz from the target frequency, which was a smaller change than the one observed in the simulation. Unlike the simulation results, the resonance frequency spectrum split into two peaks when the RF-shielded modules 16 were positioned closer than 10 mm from the phantom 14a as shown in FIG. 5a. However, when the RF coil 12 was returned to the target frequency, the frequency spectrum returned to a single peak, while the reduced Q-factor remained. When the gamma-ray shielded modules 16 were moved into the space between the RF coil loops 12, the frequency remained constant, but the Q-factor dropped. This finding is consistent with the previous studies. When both the gamma-ray and RF shielding were positioned within the RF coil 12, the resonance frequencies shifted up about 7 MHz while the Q-dropped even lower. When the RF coil 12 was re-tuned to the target frequency, the Q-factor remained low, but the splitting in the frequency spectrum was again resolved. A summary of these measurements are shown below in Table 1.

TABLE 1

Average values of the parameters of the two circular loops of the RF array coil. The frequency and Q-factors were measured without loading the coil. The SNR was calculated from the MR images of the brick phantom.

|  | Frequency (MHz) | Q-factor | Q-factor after re-tuning | SNR |
| --- | --- | --- | --- | --- |
| No shielding | 127.0 | 117.5 | — | 301.1 |
| RF shielding | 132.5 | 86.1 | 87.9 | 231.3 |
| Gamma-ray shielding | 127.0 | 82.0 | — | 219.8 |
| RF and gamma-ray shielding | 134.0 | 68.6 | 61.3 | 185.6 |

Figure 6:
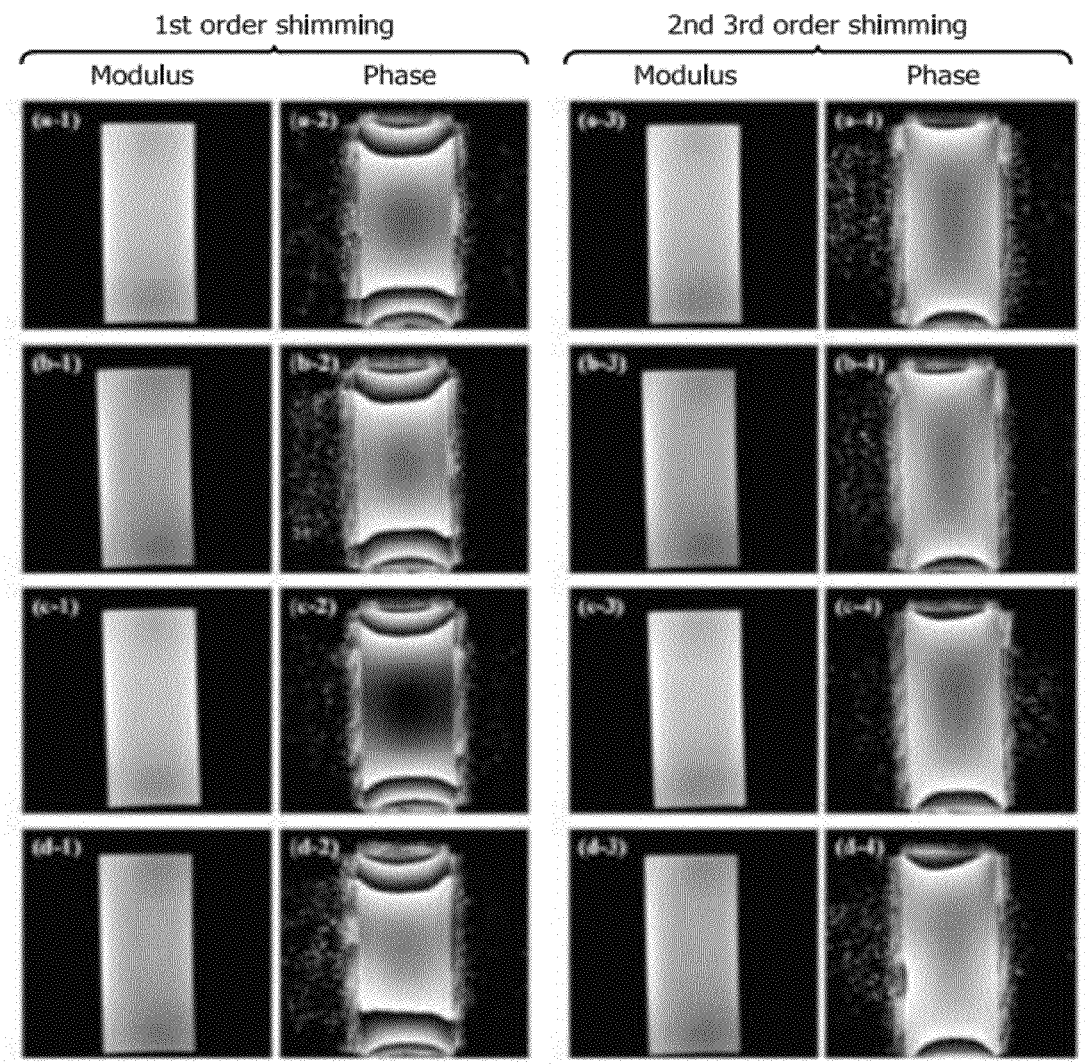

MR images of the brick phantom are shown in FIG. 6. A similar modulus image for all shielding configurations indicates that the B1 field with the phantom region was not significantly affected by the presence of the RF or gamma-ray shielding, as predicted by the simulation studies. With linear (1st) order shimming, the phase images ere also similar, except for the case with only the gamma-ray shielding. However, high (2nd and 3rd) order shimming resulted in similar and more uniform phase images for all configurations. The SNRs calculated from the modulus images acquired with high order shimming are listed in Table 1. These values parallel the changes in the Q-factor for the different shielding configurations.

Figure 7:
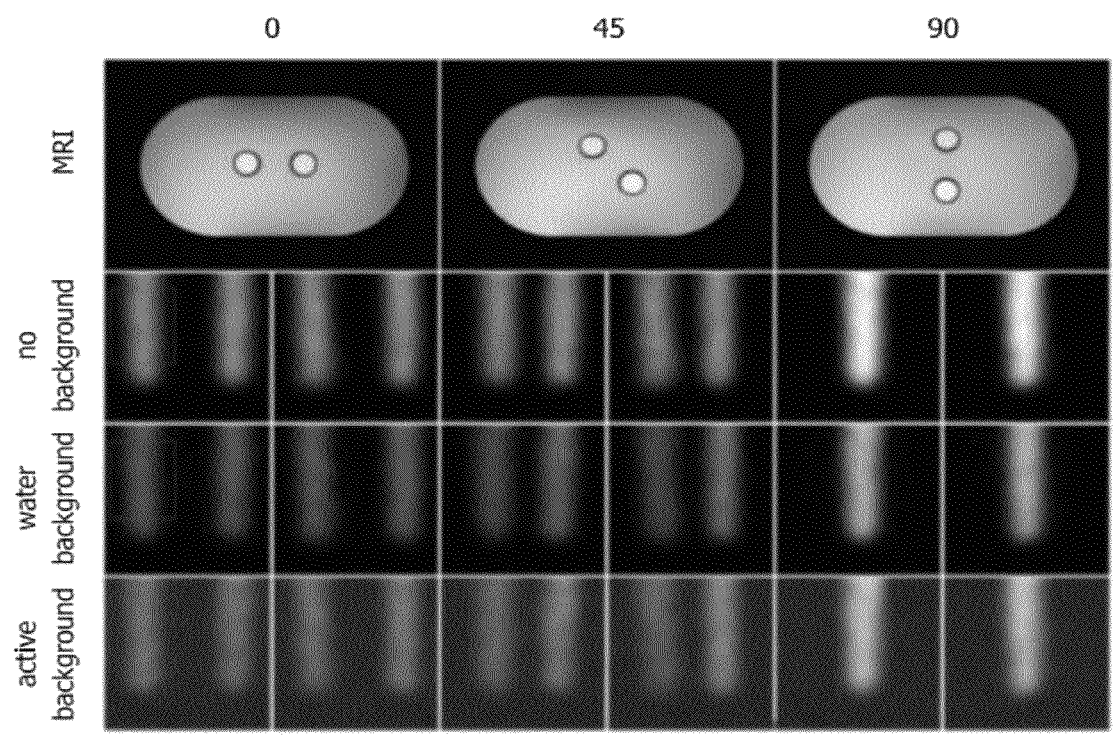
FIG. 7 are grayscale data MR and SMM images from a top detector (left ages of each column) and bottom detector (right images of each column) of a breast phantom with three different simulated compression angles for three different background configurations. Each SMM image interpolated was normalized to the maximum value of all the images. The red box denotes the region of interest (ROI) used to measure the radioactive counts.

MR and SMM images of the compressed breast phantom are shown in FIG. 7. The number of radioactive counts measured within an ROI encompassing one of the vials is listed in Table 2 below. As anticipated, the two vials 32 are distinguishable in the SMM images for the 0° and 45° orientations, but indistinguishable for the 90° orientation, thus demonstrating the importance of using the proper compression angle. The image intensity and measured activity of the vials 32 decrease as water is added to the background due to attenuation of the gamma-rays. For the 45° orientation with water background, the two vials 32 have slightly different intensities due to the different attenuating distances through the water from each vial 32 to the detector 16. The measured radioactivity within the ROI increases when radioactivity is added to the background since both the vial 32 and the background contribute to the counts measured within the ROI. Attenuation correction of the measured counts from the water background configuration was able to restore the original (no background) counts to within 2%. Subtraction of the background activity within the ROI followed by attenuation correction was able to restore the counts from the active background configuration to within 1%.

TABLE 2

Radioactive counts within the ROI of FIG. 7 for the different background configurations. MRI-based attenuation correction (AC) and background correction (BC) were used to restore the original (no background) counts from the vial.

|  | no background | water background | active background |
| --- | --- | --- | --- |
| raw counts | 59056 | 36175 | 65110 |
| with AC | — | 60242 | — |
| with BC | — | — | 35845 |
| with AC and BC | — | — | 59692 |

The results of simulation and experimental measurements demonstrate the effects of placing CZT detector modules 16 with RF and gamma-ray shielding into an RF array coil 12 for MRSMM imaging. The RF shielding introduces a shift in the resonance frequency and an increase in the $E_1$ electric field and SAR at the periphery of the test phantom 14a. The gamma-ray shielding introduces inhomogeneity in the $B_0$ field. Both shielding layers do not distort the distribution of the $B_1$ field in the region between the coil loops 12a, 12b, but do result in a decrease in the Q-factor of the RF coil 12 and the SNR of the MR images.

To avoid these adverse effects, MR and SMM imaging may be performed sequentially, where the RF coil 12 is operated without the presence of the (shielded) CZT detector modules 16. However, if simultaneous imaging is performed, various techniques may be utilized to reduce these adverse effects. To avoid manually re-tuning the RF coil 12 whenever the CZT detector modules 16 are moved within the RF coil 12, an auto-tuning method using varicap diodes may be utilized. To reduce SAR deposition, lower flip angles, shorter echo train lengths, increased inter-echo spacing, and/or longer TR values may be utilized. Similarly, rapid acquisition with relaxation enhancement (RARE) and variable-rate selective excitation (VERSE) methods may be utilized to improve MR image quality without exceeding SAR limits. The RF array coil 12 may also be adapted for use with parallel imaging techniques, which can decrease RF exposure, by reducing the number of phase-encoding steps. As previously demonstrated, distortion of the $B_0$ field by the gamma-ray shielded may be corrected through high order shimming. Finally, the drop in image SNR may be compensated by additional signal averaging at the expense of imaging time.

Despite a reduced SNR, the breast phantom experiment demonstrates that accurate MR images ay still be obtained with simultaneous MRSMM imaging.

Furthermore, the MR images were used to measure the geometry of the phantom 14a to facilitate attenuation and background correction of the radioactive counts within the ROI of the SMM images. In more complex objects, such as the human body, segmentation of the MR images into different tissue types with their corresponding attenuation coefficients and uptake values may be utilized for such corrections. This may enable accurate quantification of radiotracer uptake by suspicious lesions, which may be of clinical value.

In addition to attenuation and background corrections, combined MR and SMM imaging has several other advantages Co-registered anatomical MR images provide a reference for the SMM images, allowing for improved localization. The higher spatial resolution MR images can be utilized to improve the spatial resolution of gamma ray images through post-processing techniques such as the maximization of mutual information. Simultaneous imaging enables the use of both MRI contrast agents and radiotracers to investigate multiple biological processes at the same time.

An additional advantage of simultaneous acquisition is reduction in imaging time by eliminating the need for two separate scans. This is beneficial in a clinical setting, where scheduling, patient convenience, and cost management are significant factors. The rationale for combining MRI with gamma-ray imaging is well understood in the art.

Many alteration and modifications may be made by those having ordinary skill in the art without departing from the spirit and scope of the invention. Therefore, it must be understood that the illustrated embodiments have been set forth for the purpose of example and that they should not be taken as limiting the invention as defined by the following invention and its various embodiments.

The words used in this specification to describe the invention and its, various embodiments are to be understood not only in the sense of their commonly defined meanings, but to include by special definition in this specification structure, material or acts beyond the scope of the commonly defined meanings. Thus if an element can be understood in the context of this specification as including more than one meaning, then its use in must be understood as being generic to all possible meanings supported by the specification and by the word itself.

The definitions of the words or elements of the following invention and its various embodiments are, therefore, defined in this specification to include not only the combination of elements which are literally set forth but all equivalent structure, material or acts for performing substantially the same function in substantially the same way to obtain substantially the same result. In this sense it is therefore contemplated that an equivalent substitution of two or more elements may be made for any one of the elements in the invention and its various embodiments below or that a single element may be substituted for two or more elements in a claim.

Insubstantial changes from the claimed subject matter viewed by a person with ordinary skill in the art, now known or later devised, are expressly contemplated as being equivalently within the scope of the invention and its various embodiments. Therefore, obvious substitutions now or later known to one with ordinary skill in the art are defined to be within the scope of the defined elements.

The invention and its various embodiments are thus to be understood to include what is specifically illustrated and described above, what is conceptionally equivalent, what can be obviously substituted and also what essentially incorporates the essential idea of the invention.

We claim:

1. An apparatus for combined magnetic resonance imaging and nuclear imaging of a human breast, the apparatus comprising:
    a magnetic resonance imaging system comprising first and second RF coils positioned opposite each other along a first axis, wherein the first and second RF coils are separated from each other by an open space, and a nuclear imaging system comprising first and second nuclear detectors positioned opposite each other along a second axis, which is perpendicular to the first axis, wherein the first and second nuclear detectors are disposed within the open space, and wherein both the first and second nuclear detectors are shielded from gamma and RF radiation, such that co-registered magnetic resonance imaging and nuclear imaging can be performed simultaneously; and
    a positioning apparatus comprising first and second compression paddles configured to compress the breast being imaged within the open space between the first and second RF coils, and wherein the first and second nuclear detectors are integrated with the respective first and second compression paddles.

2. The apparatus of claim 1, wherein both the first and second nuclear detectors of the nuclear imaging system either comprise a scintigraphic single photon imager or a coincidence based positron emission mammography (PEM) detector.

3. The apparatus of claim 1, wherein the first and second nuclear detectors are integrated along an outer surface of the respective first and second compression paddles so as not to interfere with compression of the breast within the open space.

4. The apparatus of claim 1, wherein the first and second nuclear detectors comprise cadmium-zinc-telluride detectors.

5. The apparatus of claim 3, further comprising a first collimator disposed between the first compression paddle and the first nuclear detector, and a second collimator disposed between the second compression paddle and the second nuclear detector.

6. A method for breast imaging, the method comprising:
    providing an apparatus comprising a MRI system, a nuclear imaging system, and first and second compression paddles, wherein the MRI system comprises a first RF coil and a second RF coil that are positioned opposite each other along a first axis, wherein the nuclear imaging system comprises a first nuclear detector and a second nuclear detector that are positioned opposite each other along a second axis, wherein both the first nuclear detector and the second nuclear detector include a RF shield and a gamma shield, and wherein the first and second axes are perpendicular to one another;
    compressing a breast between the first and second compression paddles;
    performing MRI and nuclear imaging simultaneously with the MRI system and the nuclear imaging system respectively.

7. The method of claim 6, wherein the first and second nuclear detectors are both cadmium-zinc-telluride detectors or both position emission mammography detectors.

8. A method for imaging a human breast, the method comprising:
    performing scintimammography or positron emission mammography; and simultaneously performing MRI using a dual-modality system with a first RF coil and a second RF coil and a first nuclear detector and a second nuclear detector both detectors including a RF shield and a gamma shield, under a magnetic field produced by the RF coils, without significant mutual interference,
    wherein the first and second RF coils are positioned opposite each other and are aligned along a common axis and separated by an open space, and
    wherein the first and second nuclear detectors are positioned opposite each other and are disposed within the open space between the first and second RF coils and are oriented on a common axis perpendicular to the common axis of the first and second RF coils.

9. The method of claim 8, wherein the first and second nuclear detectors are an cadmium-zinc-telluride detectors or positron emission mammography detectors.

10. An imaging method, comprising:
- performing nuclear imaging selected from the group consisting of scintimammography or positron emission mammography, to generate a nuclear imaging data field, and simultaneously performing MRI to generate a MRI data field by using a dual-modality system with a first RF coil and a second RF coil that are positioned opposite each other along a first axis and a first nuclear detector and a second nuclear detector that are positioned opposite each other along a second axis, wherein both first and second nuclear detectors include a RF shield and a gamma shield, such that the nuclear imaging and MRI do not interfere with one another, and wherein the first and second axes are perpendicular to one another;
- combining and coregistering the nuclear imaging data field and the MRI data field to generate a composite data image; and
- recording the composite data image on a tangible medium.

* * * * *